United States Patent [19]
Podszun et al.

[11] Patent Number: 5,258,067
[45] Date of Patent: Nov. 2, 1993

[54] LIQUID FOR CONDITIONING TOOTH OR BONE SUBSTANCE

[75] Inventors: Wolfgang Podszun, Cologne; Michael Müller, Bergisch Gladbach; Jens Winkel, Cologne-Pesch; Hans-Dieter Block, Leverkusen, all of Fed. Rep. of Germany

[73] Assignee: Bayer Aktiengesellschaft, Leverkusen, Fed. Rep. of Germany

[21] Appl. No.: 996,363

[22] Filed: Dec. 23, 1992

Related U.S. Application Data

[63] Continuation of Ser. No. 666,549, Mar. 7, 1991, abandoned, which is a continuation of Ser. No. 362,625, Jun. 6, 1989, abandoned.

[30] Foreign Application Priority Data

Jun. 25, 1988 [DE] Fed. Rep. of Germany ....... 3821578

[51] Int. Cl.$^5$ ............................ C09K 3/00; A61C 5/00
[52] U.S. Cl. ................... 106/35; 433/217.1; 433/228.1
[58] Field of Search .................. 106/35; 433/215, 216, 433/217, 226, 228.1; 424/54, 55, 57; 514/121, 141, 900, 901, 108; 252/389.2, DIG. 17, 79.1; 260/998.11; 427/2; 156/625, 637; 523/109–118

[56] References Cited

U.S. PATENT DOCUMENTS

| 2,793,211 | 5/1957 | LoCicero et al. | 260/294 |
|---|---|---|---|
| 3,485,810 | 12/1969 | Tilak | 260/88.2 |
| 3,518,240 | 6/1970 | Tilak et al. | 260/88.2 |
| 3,886,205 | 5/1975 | Geffers et al. | 260/502.4 R |
| 3,962,433 | 6/1976 | Worms et al. | 514/121 |
| 3,965,024 | 6/1976 | Schnadel et al. | 252/95 |
| 4,039,513 | 8/1977 | Naarmann et al. | 260/671 A |
| 4,118,472 | 10/1978 | Gaffar et al. | 424/54 |
| 4,118,473 | 10/1978 | Gaffar et al. | 424/54 |
| 4,118,474 | 10/1978 | Gaffar et al. | 424/54 |
| 4,118,475 | 10/1978 | Gaffar et al. | 424/54 |
| 4,118,476 | 10/1978 | Gaffar et al. | 424/54 |
| 4,154,813 | 5/1979 | Kleinberg | 424/48 |
| 4,213,961 | 7/1980 | Curtis et al. | 424/54 |
| 4,215,105 | 7/1980 | Gaffar et al. | 424/57 |
| 4,224,308 | 9/1980 | Gaffar et al. | 424/49 |
| 4,224,309 | 9/1980 | Gaffar et al. | 424/54 |
| 4,259,117 | 3/1981 | Yamauchi et al. | 106/35 |
| 4,323,696 | 4/1982 | Schmitz-Josten et al. | 560/220 |
| 4,348,381 | 9/1982 | Gaffar et al. | 424/57 |
| 4,383,052 | 5/1983 | Higo et al. | 523/118 |
| 4,396,378 | 8/1983 | Orlowski et al. | 106/35 |
| 4,593,054 | 6/1986 | Asmussen et al. | 523/118 |
| 4,636,533 | 1/1987 | Janda et al. | 522/14 |
| 4,661,523 | 4/1987 | Disch et al. | 514/635 |
| 4,698,376 | 10/1987 | Asmussen et al. | 523/115 |
| 4,810,195 | 3/1989 | Asmussen et al. | 433/215 |
| 4,830,616 | 5/1989 | Okuda et al. | 433/217.1 |
| 4,879,402 | 11/1989 | Reiners et al. | 560/26 |
| 4,914,159 | 4/1990 | Bomer et al. | 525/328.2 |
| 4,937,000 | 6/1990 | Bomer et al. | 210/656 |
| 4,952,241 | 8/1990 | Reiners et al. | 106/35 |
| 4,952,614 | 8/1990 | Reiners et al. | 523/115 |
| 4,966,934 | 10/1990 | Huang et al. | 523/118 |
| 5,061,183 | 10/1991 | Nicholson | 433/228.1 |

FOREIGN PATENT DOCUMENTS

| 0161386 | 11/1985 | European Pat. Off. |
| 2229087 | 12/1973 | Fed. Rep. of Germany. |
| 2360797 | 6/1975 | Fed. Rep. of Germany. |
| 2745982 | 4/1979 | Fed. Rep. of Germany. |
| 2361865 | 3/1978 | France. |
| 51-115248 | 6/1976 | Japan. |

OTHER PUBLICATIONS

J. Dent. REs. 57, 500–505 (1978).
Scand. J. Dent.Res. 92, 480–483 (1984).
Scan. J. Dent. Res. 88, 348–351 (1980).
J. Dent Res. 63, 1087–1089 (1984).
Houben-Weyl, Methoden der organischer Chemie, vol. E20, p. 80ff, Georg Thieme Verlag Stuttgart 1987.
R. S. Baratz, J. Biomat. Applications, vol. 1, 1987, S. 316ff.
K. Eichner, "Azhnärztliche Werkstoffe und ihre Verarbeitung", vol. 2, S. 135ff, Hüthig Verlag 5, Aufl. 1985.
G. Blaschke, Chromatogr. Sci. 1988, 40, 179–198.
Zh. Org. Khim. 28, 1173 (1987).
Bull. Chem. Soc. Jap. 37, (1964), 191.

Primary Examiner—Mark L. Bell
Assistant Examiner—Margaret Einsmann
Attorney, Agent, or Firm—Sprung Horn Kramer & Woods

[57] ABSTRACT

An aqueous solution for conditioning tooth or bone substance containing phosphono carboxylic acids wherein the solution has a pH in the range 1 to 8.

4 Claims, No Drawings

LIQUID FOR CONDITIONING TOOTH OR BONE SUBSTANCE

This application is a continuation of application Ser. No. 666,549, filed Mar. 7, 1991, now abandoned, which is a continuation of application Ser. No. 362,625, filed Jun. 6, 1989, now abandoned.

The invention relates to a liquid for conditioning defective tooth or bone substance for management with plastic synthetic material.

Hardening plastic synthetic materials are used particularly in dentistry as filling materials for the management of cavities in tooth or bone substance. Preferred as hardening synthetic materials are, in general, acrylate-based fillings. However, these polymeric fillings have the disadvantage that they adhere poorly to the dentine or the bone. In order to solve this problem for example, in some cases hitherto undercuts have been effected; for this it was necessary to remove considerable amounts of fresh dentine beyond the region affected.

In order to avoid these disadvantages, the dentine or the bone has been pretreated in various ways in order to increase the adhesion of the synthetic material.

Thus, it is known to etch the dentine or the enamel surface with strong acids, for example phosphoric acid, and then to carry out the filling (Scand. J. Dental Res. 88, 348–351 (1981)). Apart from the irritant action of the strong acid in the region of the mouth, the adhesion of the filling is inadequate.

It is additionally known to pretreat the dentine with ethylenediaminetetraacetic acid (EDTA) and then to provide it with a coating agent composed of an aliphatic aldehyde or a ketone and an olefinically unsaturated monomer, for example an ester of acrylic or methacrylic acid (EP-A 0,141,324 and EP-A 0,109,057).

Liquids for conditioning tooth or bone substance have been found which contain phosphono carboxylic acids of the formula

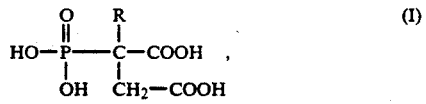

in which

R denotes hydrogen or, a $C_1$ to $C_{12}$-alkyl radical, $C_2$ to $C_{12}$-alkenyl, $C_5$ to $C_8$-cycloalkyl, $C_6$ to $C_{12}$-aryl or $C_7$ to $C_{12}$-aralkyl which are optionally substituted by hydroxyl, carboxyl and/or the groups

and/or —COOR',
where R' stands for hydrogen or $C_1$ to $C_{12}$-alkyl and/or the salts thereof, in aqueous solution, the solution having a pH in the range 1 to 8.

The new liquids according to the invention condition tooth or bone substance before coating with a primer or liner. A plastic synthetic material applied to tooth or bone substance pretreated in this way undergoes durable bonding.

Within the scope of the present invention the radicals have the following meaning in general:

Alkyl stands in general for a straight-chain or branched hydrocarbon radical having 1 to 12 carbon atoms. Lower alkyl having 1 to, say, 6 carbon atoms, is preferred. Examples which may be mentioned are methyl, ethyl, propyl, isopropyl, butyl, isobutyl, pentyl, isopentyl, hexyl and isohexyl. Methyl and ethyl are particularly preferred.

Alkenyl stands in general for a straight-chain or branched hydrocarbon radical having 2 to 12 carbon atoms and one or two, preferably one, double bond. Lower alkenyl having 2 to, say, 6 carbon atoms is preferred. Examples which may be mentioned are vinyl, allyl, propenyl, isopropenyl, butenyl, isobutenyl, pentenyl, isopentenyl, hexenyl and isohexenyl.

Cycloalkyl stands in general for a cyclic hydrocarbon radical having 5 to 8 carbon atoms. Examples which may be mentioned are cyclopentyl, cyclohexyl, cycloheptyl and cyclooctyl. Cyclopentyl and cyclohexyl are particularly preferred.

Aryl stands in general for an aromatic radical having 6 to, say, 12 carbon atoms. Preferred aryl radicals are phenyl, naphthyl and biphenylyl.

Aralkyl stands in general for an aryl radical which has 7 to 12 carbon atoms and is bonded via an alkyl chain. Preferred aralkyl radicals have 1 to 5 carbon atoms in the aliphatic and 6 to 12 carbon atoms in the aromatic moiety. Examples which may be mentioned are the following aralkyl radicals: benzyl, naphthylmethyl, phenethyl and phenylpropyl.

Preferred within the scope of the present invention are phosphono carboxylic acids of the formula (I) in which R denotes hydrogen or $C_1$ to $C_6$-alkyl which is optionally substituted by —COOH or

The following phosphono carboxylic acids may be mentioned by way of example:

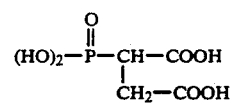

phosphonosuccinic acid (PSA)

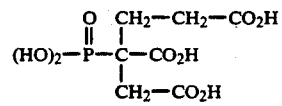

2-phosphonobutane-1,2,4-tricarboxylic acid (PBTA) and

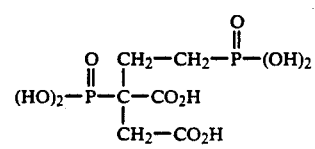

2,4-diphosphonobutane-1,2-dicarboxylic acid (DPBD).

Salts of the phosphono carboxylic acids according to the invention which may be mentioned in particular are the alkali metal salts, preferably the sodium and potassium salts.

The proportion of the phosphono carboxylic acids or the salts thereof in the liquids according to the invention for conditioning tooth or bone substances is determined by the pH.

The pH is, according to the invention, in the range 1 to 8, preferably in the range 2 to 7, particularly preferably in the range 2.5 to 5.

It is possible to adjust the pH by addition of alkali metal hydroxide solutions, for example of sodium hydroxide or potassium hydroxide. The pH can be measured in a manner known per se, for example using suitable indicators or using potentiometric measurement methods (Ullmann, Volume 5, 926 to 936 (1980)).

The aqueous liquids according to the invention for conditioning tooth or bone substances may contain as further ingredient organic carboxylic acids having a pKa below 5, preferably in the range 1 to 4. The following carboxylic acids may be mentioned by way of example: pyruvic acid, citric acid and oxalic acid.

Furthermore, the liquids according to the invention may contain amphoteric amino compounds having a pKa of 9.0 to 10.6 and $pK_B$ of 11.5 to 12.5.

Amphoteric amino compounds of the formula (II)

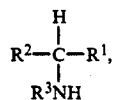

in which $R^1$ stands for a carboxyl group, $R^2$ denotes hydrogen or a lower alkyl radical which is optionally substituted by hydroxyl, mercapto, methylthio, carboxyl, carbonamide, amino phenyl, hydroxy-phenyl or the groups

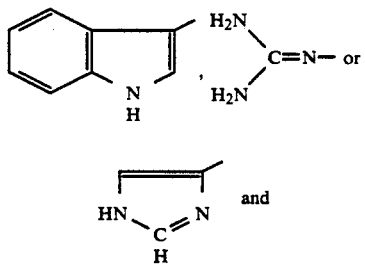

$R^3$ denotes hydrogen or phenyl, or $R^1$ and $R^3$ can be connected by a propylene radical, or in which $R^1$ represents hydrogen, $R^2$ denotes the group

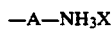

—A—NH$_3$X

A stands for an alkylene radical having 1 to 6 carbon atoms, and

X stands for halogen, and $R^3$ denotes hydrogen, may be mentioned as preferred.

The following amphoteric amino compounds may be mentioned by way of example: glycine, serine, threonine, cysteine, tyrosine, asparagine, glutamine, alanine, valine, leucine, isoleucine, protine, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride and butylenediamine hydrobromide.

Particularly preferred amphoteric amino compounds are glycine, phenylalanine, lysine and ethylenediamine hydrochloride.

It is also possible to add complexing agents such as ethylenediaminetetraacetic acid (EDTA) and salts derived therefrom.

The aqueous liquids according to the invention for conditioning may contain, for example, 1 to 50 parts by weight of phosphono carboxylic acids, or salts derived therefrom, 0 to 15 parts by weight of organic carboxylic acids, 0 to 10 parts by weight of amphoteric amino compounds, 0 to 10 parts by weight of ethylenediaminetetraacetic acid, or salts derived therefrom.

A process for the preparation of liquids for conditioning tooth or bone substances has also been found, which is characterized in that an aqueous solution of a phosphono carboxylic acid of the formula

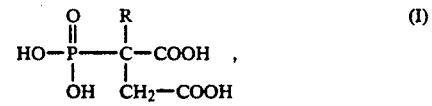

in which

R denotes hydrogen or, a $C_1$ to $C_{12}$ alkyl radical, $C_2$ to $C_{12}$-alkenyl, $C_5$ to $C_8$-cycloalkyl, $C_6$ to $C_{12}$-aryl or $C_7$ to $C_{12}$-aralkyl which are optionally substituted by hydroxyl, carboxyl and/or the groups

and/or —COOR', where R' stands for hydrogen or $C_1$ to $C_{12}$-alkyl and/or the salts thereof, is prepared with the pH being maintained in the range 1 to 8.

The pH is in general adjusted by addition of alkali metal hydroxide solutions, for example of sodium hydroxide or potassium hydroxide.

In the preparation of the liquids according to the invention the components are in general mixed with vigorous stirring. The components are mixed in general at room temperature, for example in the temperature range 0° to 30° C.

The conditioning liquids according to the invention can furthermore contain thickening agents or surface-active substances in order to adjust the viscosity thereof or the wetting behaviour thereof to meet special requirements. It is particularly beneficial to add polyvinylpyrrolidone or polyethylene glycols.

When used, the liquids according to the invention are applied to the defective tooth or bone substance, for example into a cavity. Cavities in the enamel or dentine may be mentioned as preferred in this connection.

After the liquids according to the invention have been applied they are in general dried, for example with warm air.

Before the management with the plastic synthetic material of the defective tooth or bone substance, and after the conditioning with the liquids according to the invention, preferably coating with a primer is carried out.

Primers which may be mentioned in particular in this connection are those described in EP-A 0,141,324 and EP-A 0,199,057.

Particularly preferred primers are those which contain an aldehyde or a ketone and an unsaturated monomer with active hydrogen.

Aldehydes which may be mentioned in this connection are formaldehyde, compounds which are able to liberate formaldehyde, and acetaldehyde, propionaldehyde, butyraldehyde and glutaraldehyde. Glutaraldehyde is particularly preferred.

Ketones which may be mentioned in this connection are cyclopentanone, benzophenone, cyclohexanone, 2,4-pentanedione and camphorquinone. Camphorquinone is particularly preferred.

Olefinically unsaturated monomers with active hydrogen (Bronsted acid) which may be mentioned are acrylic esters, methacrylic esters and acrylic acid and methacrylic acid urethanes having OH, $NH_2$, NH, SH or PH groups. Hydroxyethyl methacrylate is particularly preferred.

Particularly preferred primers are those which contain 1 to 50% by weight of an aliphatic aldehyde having 1 to 20 carbon atoms and 5 to 80% by weight of an olefinically unsaturated monomer with at least one active hydrogen atom in the form of OH, $NH_2$ or SH groups and, where appropriate, water and/or a toxicologically acceptable organic solvent. The hardening synthetic materials are essentially determined by the area of use. Thus, for example, it is possible in dentistry to use for the polymerization only monomers which are physiologically acceptable and are able to polymerize in the region of the mouth. Monomers of this type for dental fillings are known per se (for example Ullmanns Enzyklopädie der Technischen Chemie (Ullmann's Encyclopedia of Industrial Chemistry)).

Examples of synthetic materials which may be mentioned are compositions of acrylate and/or methacrylate monomers, suitable catalysts, starters, accelerators and fillers.

Surprisingly, the conditioning of the defective tooth or bone substance with the liquids according to the invention results in a basis for management with synthetic materials which ensures high durability and strength of the repair.

EXAMPLE 1

Conditioning Liquids

Solutions with the concentrations and PH values indicated below were prepared from phosphonosuccinic acid (PSA), glycine and water. The pH was adjusted in Examples B-D with 4N NAOH.

| Example No. | PSA [mol/l] | Glycine [mol/l] | pH |
|---|---|---|---|
| 1 A | 2.40 | 0.057 | <1 |
| 1 B | 0.44 | 0.057 | 3.5 |
| 1 C | 0.44 | 0.057 | 6.0 |
| 1 D | 0.44 | 0.057 | 8.0 |
| 1 E | 2.40 | 0.316 | 3.5 |

EXAMPLE 2

Conditioning Liquids

Solutions with the concentrations and pH values indicated below were prepared from 2-phosphonobutane-1,2,4-tricarboxylic acid (PBTA), glycine and water. The pH was adjusted in Examples B-D with 4N NAOH.

| Example No. | PBTA [mol/l] | Glycine [mol/l] | pH |
|---|---|---|---|
| 2 A | 2.3 | 0.057 | <1 |
| 2 B | 0.46 | 0.057 | 3.5 |
| 2 C | 0.46 | 0.057 | 6.0 |
| 2 D | 0.46 | 0.057 | 8.0 |
| 2 E | 2.1 | 0.323 | 3.5 |

EXAMPLE 3

(Test of Strength of Bonding)

In the example, the strength of bonding (tensile strength) between dentine or enamel and a commercially available synthetic filling composition is measured.

Used for the test are human teeth which have been extracted and stored under moist conditions. The teeth are embedded in epoxy resin by casting; a fiat surface is produced by wet grinding. Final grinding is carried out with carborundum paper 1000.

The surface is then treated with a liquid from Example 1 or 2 for 60 seconds in each case. The treated area is then rinsed with distilled water and dried with air.

Subsequently the surface which has been conditioned with the liquids of Examples 1 or 2 is treated for 60 seconds with the coating agent composed of 5% by weight glutaraldehyde, 36% by weight hydroxyethyl methacrylate and 59%. by weight water. The surface is then dried with air.

To prepare a specimen for measurement of the strength of bonding, a cylindrical spat Teflon mould is clamped onto the treated surface described above (Scand. J. Dent. Res. 88, 348 to 351 (1981)).

A thin film composed of a solution of 65% by weight bisphenol A diglycidyl methacrylate, 34.3% by weight of triethylene glycol dimethacrylate, 0.2% by weight of camphorquinone and 0.5% by weight of sulphonamide are applied into the mold, and then a light-activated synthetic filling material (Lumifor, sayer AG) is introduced. Hardening is carried out with a photopolymerization Lamp for 60 seconds. After a further 15 minutes, the Teflon mold is removed, and the strength of bonding is determined using an Instron tensile test apparatus (Scand. J. Dent. Res. 88, 348 to 351 (1981)) with a traction rate of 5 mm/min.

The tensile strengths on dentine measured thereby were as follows:

| Conditioning liquid | Tensile strength [N/mm$^2$] |
|---|---|
| 1 A | 6.1 ± 0.4 |
| 1 B | 17.3 ± 2.9 |
| 1 C | 20.4 ± 2.3 |
| 1 D | 13.9 ± 3.1 |
| 1 E | 17.5 ± 1.2 |
| 2 A | 6.0 ± 1.7 |
| 2 B | 17.6 ± 1.7 |
| 2 C | 16.7 ± 0.6 |

-continued

| Conditioning liquid | Tensile strength [N/mm$^2$] |
| --- | --- |
| 2 D | 17.8 ± 3.1 |
| 2 E | 18.1 ± 4.0 |

EXAMPLE 4

A solution with the following composition was prepared from 2,4-diphosphonobutane-1,2-dicarboxylic acid (DPBD), glycine, 4N NaOH and water:

| DPBD [mol/l] | Glycine [mol/l] | pH |
| --- | --- | --- |
| 0.45 | 0.057 | 3.5 |

The strength of bonding to enamel and dentine was measured by the method described in Example 3. The figures obtained were as follows:
Enamel: 14.3 N/mm$^2$   Dentine: 13.5 N/mm$^2$

EXAMPLE 5

Aqueous conditioning liquids were prepared from 2-phosphonobutane-1,2,4-tricarboxylic acid (PBTA), citric acid (CA), EDTA magnesium salt (Mg EDTA) and polyethylene glycol 4000 (PEG), and the strengths of bonding were determined as in Example 3.

| Example No. | 5 A | 5 B |
| --- | --- | --- |
| PBTA [% by wt.] | 1 | 5 |
| MgEDTA [% by wt.] | 1 | 1 |
| CA [% by wt.] | 5 | 5 |
| PEG [% by wt.] | 10 | 10 |
| Strength of bonding to dentine [N/mm$^2$] | 17.7 ± 1.4 | 19.8 ± 2.7 |
| Strength of bonding to enamel [N/mm$^2$] | 15.1 ± 4.7 | 16.0 ± 3.7 |

What is claimed is:

1. A method for increasing the adhesion of a plastic synthetic dental material applied to defective tooth of dentine substance, said method comprising treating the defective tooth or dentine substance with an aqueous solution prior to applying the plastic synthetic dental material to the defective tooth or dentine substance, said aqueous solution containing at least one phosphono carboxylic acid of the formula

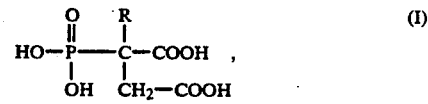

wherein
R denotes H, —CH$_2$CH$_2$COOH or —CH$_2$CH$_2$PO(OH)$_2$, or the salts thereof, in an amount of the phosphono carboxylic acid effective to increase the adhesion of the plastic synthetic dental material to the defective tooth or dentine material, the aqueous solution also having a pH in the range 1 to 8.

2. The method according to claim 1, wherein the aqueous solution contains an effective complexing amount of ethylenediaminetetraacetic acid or a salt thereof.

3. The method according to claim 2, wherein the defective tooth or dentine substance is coated with a primer after application of the aqueous solution but before application of the plastic synthetic dental material, said primer being selected from the group consisting of primers containing 1–50% by weight of an aliphatic aldehyde having 1–20 carbon atoms and 5–80% by weight of an olefinically unsaturated monomer with at least one active hydrogen in the form of OH, NH$_2$, or SH groups.

4. The method according to claim 1, wherein the plastic synthetic dental composition is a composition containing (a) acrylate or methacrylate monomers or both (b) catalysts, starters, accelerators, and fillers.

* * * * *

UNITED STATES PATENT AND TRADEMARK OFFICE
CERTIFICATE OF CORRECTION

PATENT NO. : 5,258,067
DATED : November 2, 1993
INVENTOR(S) : Podszun, et al.

It is certified that error appears in the above-indentified patent and that said Letters Patent is hereby corrected as shown below:

Col. 8, line 3    Delete " of " and substitute -- or --

Col. 8, line 40   After " both " insert -- and --

Signed and Sealed this

Fourteenth Day of May, 1996

Attest:

BRUCE LEHMAN

Attesting Officer    Commissioner of Patents and Trademarks